US011331420B2

(12) United States Patent
Ewusi-Emmim

(10) Patent No.: US 11,331,420 B2
(45) Date of Patent: May 17, 2022

(54) APPARATUS FOR FLUID DELIVERY AND LACTATION STIMULATION

(71) Applicant: NIPA YE, LLC, Salt Lake City, UT (US)

(72) Inventor: Nana Ewusi-Emmim, Salt Lake City, UT (US)

(73) Assignee: NIPA YE, LLC, Salt Lake City, UT (US)

( * ) Notice: Subject to any disclaimer, the term of this patent is extended or adjusted under 35 U.S.C. 154(b) by 74 days.

(21) Appl. No.: 16/378,349

(22) Filed: Apr. 8, 2019

(65) Prior Publication Data

US 2019/0336662 A1 Nov. 7, 2019

Related U.S. Application Data

(60) Provisional application No. 62/654,437, filed on Apr. 8, 2018.

(51) Int. Cl.
| A61M 1/06 | (2006.01) |
| A61J 15/00 | (2006.01) |
| A61M 25/02 | (2006.01) |
| A61M 39/24 | (2006.01) |
| A61J 1/10 | (2006.01) |

(52) U.S. Cl.
CPC .......... *A61M 1/068* (2014.02); *A61J 15/0003* (2013.01); *A61J 15/0026* (2013.01); *A61J 15/0053* (2013.01); *A61M 1/062* (2014.02); *A61M 25/02* (2013.01); *A61J 1/10* (2013.01);
(Continued)

(58) Field of Classification Search
CPC .................. A61M 1/068; A61M 39/24; A61M 2209/088; A61M 2210/1007; A61M 2205/076; A61M 2025/0253; A61M 2025/026; A61M 1/062; A61J 15/0003; (Continued)

(56) References Cited

U.S. PATENT DOCUMENTS

| 3,757,784 A | 9/1973 | Avery |
| 4,687,466 A * | 8/1987 | Larsson ................. A61J 9/00 |
| | | 215/11.4 |

(Continued)

FOREIGN PATENT DOCUMENTS

| EP | 3095432 A1 * | 11/2016 | ............. A61J 13/00 |
| EP | 3095432 A1 | 11/2016 | |
| WO | 2016185020 A1 | 11/2016 | |

OTHER PUBLICATIONS

Simply Hike, Camelbak Hydrobak 1,5L Hydration Pack, https://www.youtube.com/watch?v=juByV_647JM, May 9, 2014, (Year: 2014).*

(Continued)

Primary Examiner — Nathan R Price
Assistant Examiner — Anh Bui
(74) Attorney, Agent, or Firm — Snell & Wilmer L.L.P.

(57) ABSTRACT

The present invention provides a supplemental nutrition apparatus. The supplemental nutrition apparatus may comprise a reservoir coupled to and in fluid communication with a fluid passageway, wherein the fluid passageway is configured to communicate fluid from the reservoir to a fluid passageway outlet, and a support element configured to engage a user, to at least partially support the fluid passageway, and to position the fluid passageway outlet proximate to the user's nipple.

16 Claims, 22 Drawing Sheets

(52) U.S. Cl.
CPC ....... *A61M 39/24* (2013.01); *A61M 2209/088* (2013.01); *A61M 2210/1007* (2013.01)

(58) Field of Classification Search
CPC .... A61J 1/10; A61J 15/0011; A61J 115/0053; A61J 15/0026
See application file for complete search history.

(56) References Cited

U.S. PATENT DOCUMENTS

| | | | |
|---|---|---|---|
| 4,740,196 A | 4/1988 | Powell | |
| 5,474,193 A * | 12/1995 | Larsson | A61J 9/00 215/11.4 |
| 5,514,166 A * | 5/1996 | Silver | A61M 1/062 604/74 |
| 5,601,199 A * | 2/1997 | Marty | A61J 9/00 215/11.1 |
| 8,833,575 B2 | 9/2014 | Fave-Lesage | |
| 9,107,991 B1 * | 8/2015 | Frere | A61M 1/06 |
| 10,194,701 B1 * | 2/2019 | Tufts | A61M 25/02 |
| 2004/0060888 A1 * | 4/2004 | Ahn | A61J 9/00 215/11.1 |
| 2005/0266770 A1 * | 12/2005 | Henricksen | A41C 3/0007 450/1 |
| 2006/0129127 A1 | 6/2006 | Ruth et al. | |
| 2009/0166481 A1 * | 7/2009 | Chen | A61J 9/0638 248/102 |
| 2011/0259847 A1 * | 10/2011 | Cox | A61J 9/04 215/391 |
| 2011/0270164 A1 * | 11/2011 | Bane | A61J 13/00 604/76 |
| 2013/0270140 A1 | 10/2013 | Tronson | |
| 2016/0120763 A1 | 5/2016 | Conner | |
| 2018/0326130 A1 * | 11/2018 | Thompson | A61M 1/066 |

OTHER PUBLICATIONS

PCT; International Search Report and Written Opinion dated Jul. 5, 2019 in the International Application No. PCT/US2019/026391.

* cited by examiner

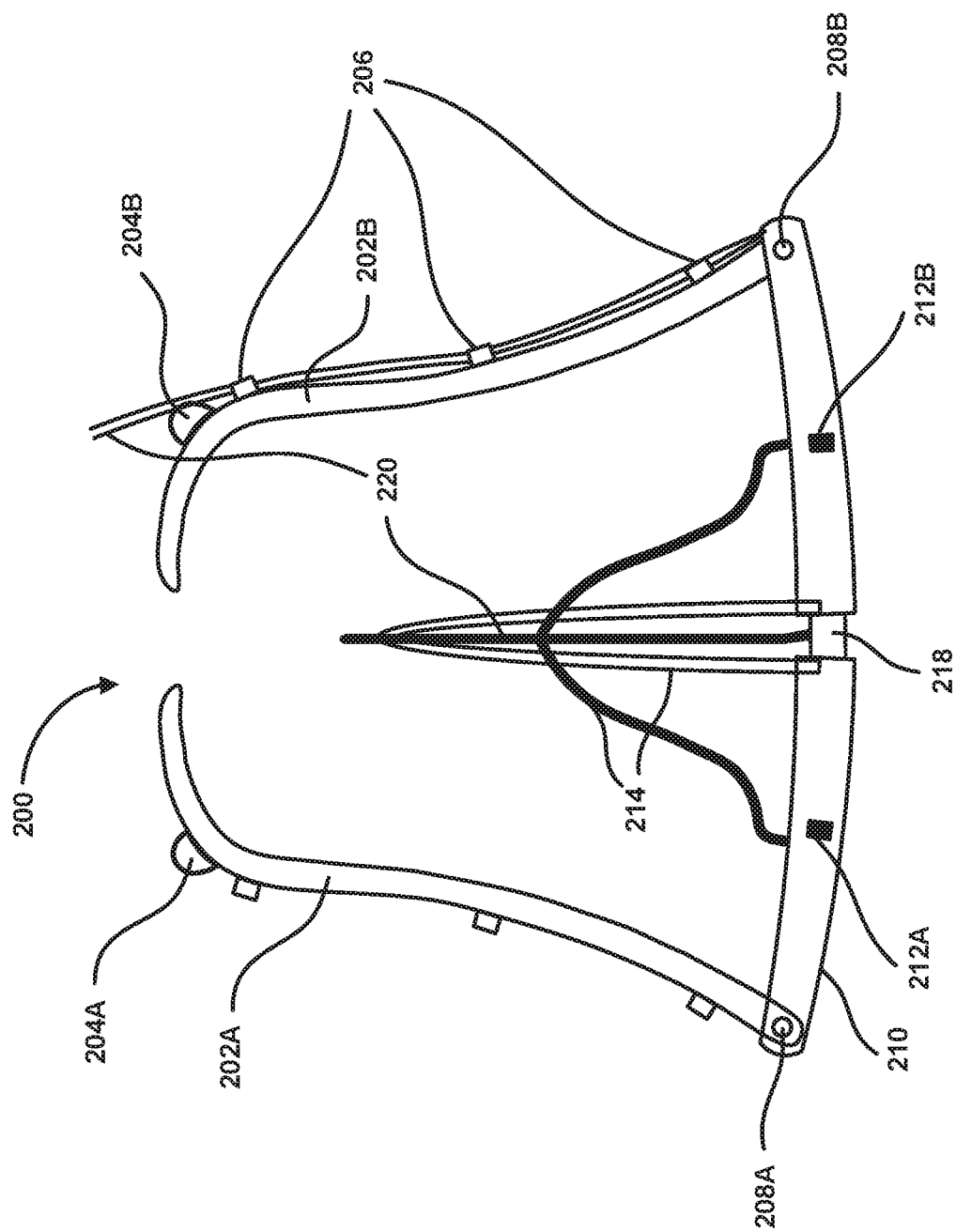

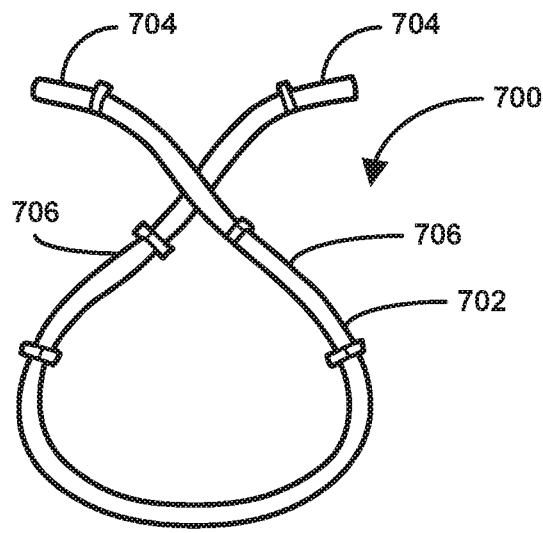
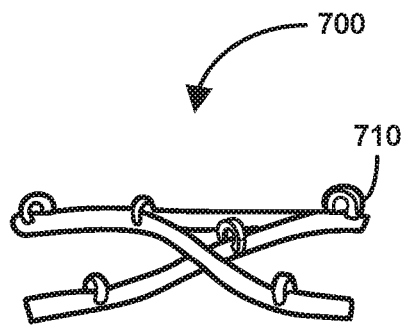
FIG. 6A
FIG. 6B
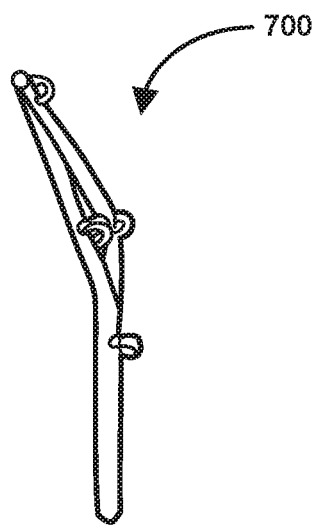
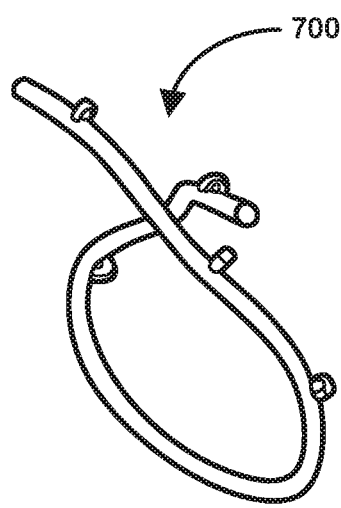
FIG. 6C
FIG. 6D

APPARATUS FOR FLUID DELIVERY AND LACTATION STIMULATION

CROSS REFERENCE TO RELATED APPLICATION

This non-provisional patent application claims priority to, and the benefit of, U.S. Provisional Patent Application No. 62/654,437, filed on Apr. 8, 2018, entitled "APPARATUS FOR FLUID DELIVERY AND LACTATION STIMULATION," which is incorporated herein by reference in its entirety.

FIELD OF THE INVENTION

The present disclosure relates generally to an apparatus for fluid delivery and lactation stimulation, and more specifically, to a supplemental nutrition apparatus for simultaneous fluid delivery and lactation stimulation.

BACKGROUND

Some women struggle to produce breast milk immediately after childbirth and often continue to struggle producing sufficient quantities of breast milk thereafter to adequately provide for their newborn's nutritional needs. Providing supplemental nutrition may cause a decrease in the mother's natural milk supply if the supplemental nutrition delivery methods (for example, bottle feeding) does not stimulate the mother's breast.

Existing supplemental nutrition systems utilize capillary tubes to deliver fluid near the mother's nipple, such that both the nipple and capillary tube are drawn into the child's mouth during latching. However, these existing systems require manual placement, positioning, and retention of such capillary tubes during use, while the mother simultaneously holds her infant, bulky portions of the supplemental nutrition system, the supplemental nutrition fluid, excess tubing, clothing, and/or other items. Use of such existing systems is difficult, and any movement of the capillary tube away from the mother's breast can distract the child and/or prevent the child from simultaneously receiving supplemental nutrition and stimulating the mother's breast. The presence of excess capillary tube at or near the mother's nipple, can cause the child to grasp the capillary tube and/or lose interest in feeding. Use of adhesive materials directly on the latching are to position and/or retain the capillary tube near the mother's nipple can deter latching due to the taste or texture of the adhesive materials and/or result in the child ingesting the adhesive materials.

Accordingly, there is a need for an improved supplemental nutrition apparatus.

SUMMARY

A supplemental nutrition apparatus is disclosed herein, the supplemental nutrition apparatus comprising a reservoir coupled to and in fluid communication with a fluid passageway, wherein the fluid passageway is configured to communicate fluid from the reservoir to a fluid passageway outlet, and a support element configured to engage a user, to at least partially support the fluid passageway, and to position the fluid passageway outlet proximate to the user's nipple.

In various embodiments, the supplemental nutrition apparatus further comprises at least one support frame configured to removably secure the supplemental nutrition apparatus to the user's breast. In various embodiments, the at least one support frame comprises a unitary support frame. In various embodiments, the supplemental nutrition apparatus further comprises at least one fluid passageway support eyelet coupled to the at least one support frame. In various embodiments, the reservoir comprises a reservoir outlet configured to communicate fluid from the reservoir to the fluid passageway. In various embodiments, the reservoir further comprises at least one guide hook. In various embodiments, the reservoir further comprises a reservoir mounting element. In various embodiments, the reservoir further comprises a check valve. In various embodiments, the supplemental nutrition apparatus further comprises an attachment element disposed on the reservoir and configured to removably couple the supplemental nutrition apparatus to the user.

A supplemental nutrition apparatus is disclosed herein, the supplemental nutrition apparatus comprising a support element belt comprising an elongated central portion disposed between a first belt attachment and a second belt attachment, and at least one fluid passageway fastener disposed on the elongated central portion, wherein the support element belt is configured to removably secure the supplemental nutrition apparatus to the user.

In various embodiments, the supplemental nutrition apparatus further comprises at least one fluid passageway support eyelet disposed on the support element belt. In various embodiments, the at least one fluid passageway fastener comprises an aperture disposed in and defined by the elongated central portion. In various embodiments, the at least one fluid passageway fastener is configured to be disposed in a child's mouth during use of the supplemental nutrition apparatus. In various embodiments, the first belt attachment and the second belt attachment comprise an adhesive disposed on a back side of the support element belt. In various embodiments, the support element belt is configured to adhere directly to a user's breast. In various embodiments, the supplemental nutrition apparatus further comprises a unitary support frame, wherein the first belt attachment and the second belt attachment comprise at least one of apertures, clips, clasps, and hooks, and wherein the first belt attachment and the second belt attachment are configured to couple the support element belt to the support frame.

A supplemental nutrition apparatus is disclosed herein, the supplemental nutrition apparatus comprising a reservoir coupled to and in fluid communication with a fluid passageway, wherein the fluid passageway is configured to communicate fluid from the reservoir to a fluid passageway outlet, and a support element configured to engage a user, to at least partially support the fluid passageway, and to position the fluid passageway outlet proximate to the user's nipple, wherein the support element comprises a support element belt comprising an elongated central portion disposed between a first belt attachment and a second belt attachment, and at least one fluid passageway fastener disposed on the elongated central portion, wherein the support element belt is configured to removably secure the supplemental nutrition apparatus to the user.

In various embodiments, the reservoir comprises a reservoir outlet configured to communicate fluid from the reservoir to the fluid passageway. In various embodiments, the reservoir further comprises at least one guide hook. In various embodiments, the reservoir further comprises a reservoir mounting element.

This summary of the disclosure is not intended to describe each illustrated embodiment or every possible implementation of the disclosure. Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the disclosure will become more fully apparent from the following description and appended claims, or may be learned by the practice of the invention as set forth hereinafter.

BRIEF DESCRIPTION OF THE DRAWINGS

The accompanying drawings are included to provide a further understanding of the present disclosure and are incorporated in, and constitute a part of, this specification, illustrate various embodiments, and together with the description, serve to explain the principles of the disclosure.

FIGS. 2A-2G illustrate perspective views of a support element, in accordance with various embodiments.

FIGS. 6A-6D illustrate various perspective views of a portion of a support element, in accordance with various embodiments.

DETAILED DESCRIPTION

Figure 1:
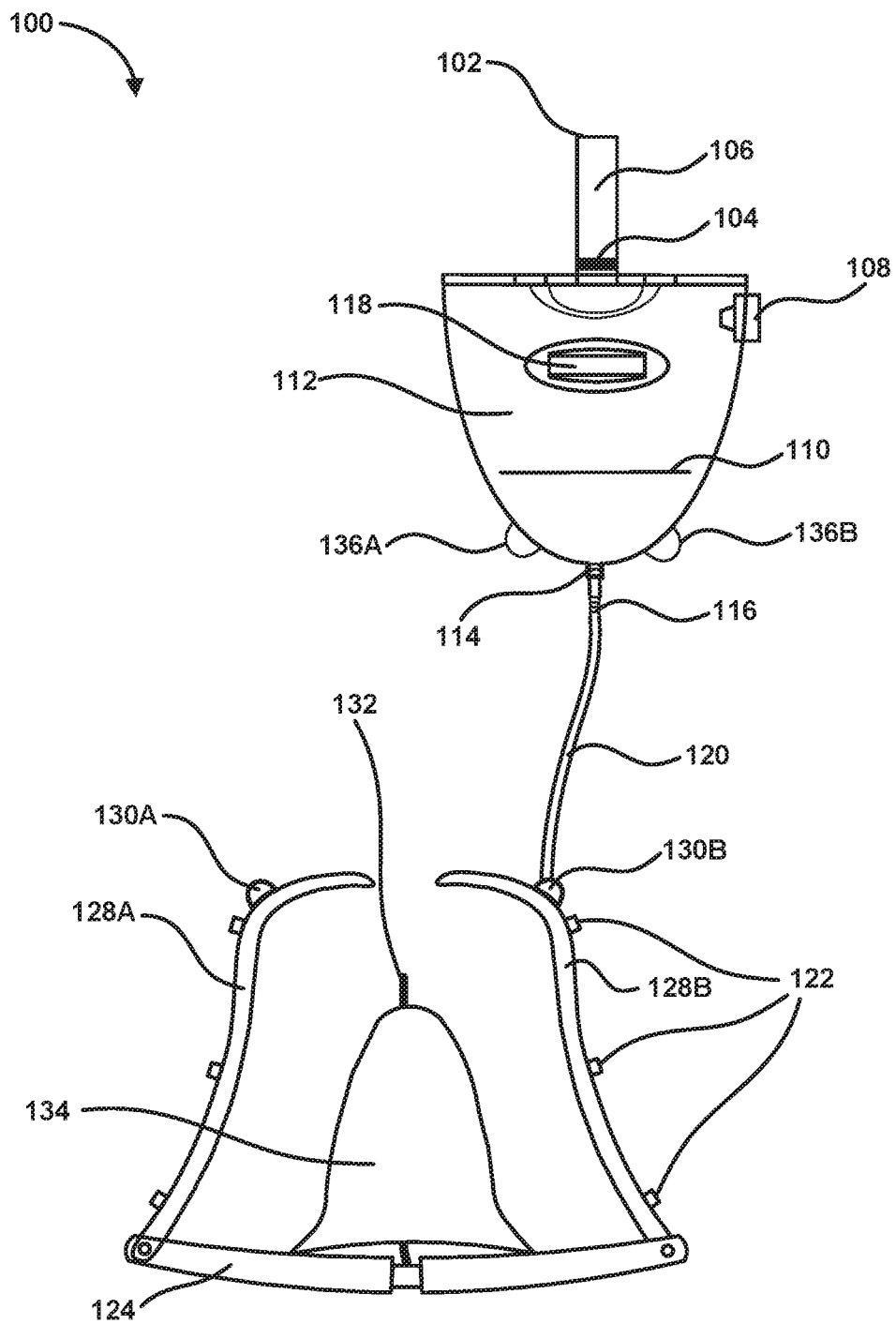
FIG. 1 illustrates a perspective view of a supplemental nutrition apparatus, in accordance with various embodiments.

The detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that logical, chemical, and mechanical changes may be made without departing from the spirit and scope of the disclosure. Thus, the detailed description herein is presented for purposes of illustration only and not of limitation.

For example, the steps recited in any method or process description included herein may be executed in any order and are not necessarily limited to the order presented. Furthermore, any reference to singular includes plural embodiments, and any reference to more than one component or step may include a singular embodiment or step. Also, any reference to attached, fixed, connected, or the like may include permanent, removable, temporary, partial, full, and/or any other possible attachment option. Additionally, any reference to without contact (or similar phrases) may also include reduced contact or minimal contact.

For example, in the context of the present disclosure, devices and methods may find particular use in connection with infant breastfeeding supplementation. However, various aspects of the disclosed embodiments may be adapted for use in nutrition supplementation for animals, premature babies, toddlers, children, disabled persons, or other uses. As such, numerous applications of the present disclosure may be realized.

The supplemental nutrition apparatus disclosed herein delivers fluid nutrition to an infant in a manner that also stimulates the breast to promote milk production. More specifically, the disclosed supplemental nutrition apparatus delivers fluid nutrition using a reservoir system and a fluid passageway while also stimulating lactation by positioning the fluid passageway outlet within proximity of the user's breast. In some embodiments, a user may fill at least a portion of a reservoir with nutritional fluid (for example, formula, previously pumped breast milk, etc.) using an access point. The user may elevate the position of the reservoir above the user's breast using an adjuster and attachment element. The user may interface the support element with the breast that the user wants to be stimulated. The user may position a fluid passageway outlet proximate to the user's nipple and/or at the user's areola. The user may feed an infant through the fluid passageway outlet while the infant simultaneously stimulates the user's breast tissue to promote lactation. In some embodiments, the infant consumes milk from the mother's breast as well as the fluid nutrition from the reservoir of the apparatus. In other embodiments, the infant may only consume fluid from the reservoir of the apparatus.

The supplemental nutrition apparatus may utilize a reservoir system, fluid passageway, and support components to facilitate delivering fluid nutrition to a newborn infant while simultaneously stimulating the user's breast to promote breast milk production. More specifically, a reservoir system configured to output fluid may operably connect to a fluid passageway. A portion of the fluid passageway may be supported within a support element. The support element may be configured to engage a user of the apparatus to secure the fluid passageway in a fixed position during use. The fluid passageway may include a fluid passageway outlet configured to output fluid proximate to the user's nipple and/or at the user's areola to deliver fluid nutrition to an infant. Because the infant consumes the fluid proximate to the user's nipple and/or areola, the infant's physical contact with the user during consumption may act to stimulate the user's breast to promote breast milk production.

The supplemental nutrition apparatus may comprise optionally separable components, including a reservoir, a fluid passageway, and a support element. However, in various embodiments, the reservoir is integral to, and/or co-molded, with the fluid passageway. In various embodiments, the fluid passageway is integral to, and/or co-molded with, the support element. In various embodiments, the reservoir, the fluid passageway, and the support element are integral to, and co-molded with, one another.

As may be used herein, directional terms such as back, front, lateral, medial, top, bottom, etc. should be understood in the context of the supplemental nutritional apparatus as worn by a user. For example, the term back refers to the surfaces of a would abut and interface with the user during use of the supplemental nutrition apparatus; the term top refers to a portion of the supplemental nutrition apparatus that it closer to a user's head than another portion of the supplemental nutrition apparatus.

FIG. 1 illustrates an embodiment of a supplemental nutrition apparatus 100 for fluid delivery and lactation stimulation. In one embodiment, the supplemental nutrition apparatus 100 may comprise an attachment element 102, an adjuster 104, a support strap 106, a check valve 108, an access point 110, a reservoir 112, a reservoir outlet 114, a fluid passageway inlet 116, a reservoir clip 118, a fluid passageway 120, a plurality of fluid passageway support eyelets 122, a support structure 124, support frames 128a, 128b having support element clips 130a, 130b, a fluid passageway outlet 132, a fluid passageway outlet support 134, and/or reservoir clips 136a, 136b. The reservoir 112 may be in fluid communication with the fluid passageway 120. For example, the reservoir 112 may include a reservoir outlet 114 that may detachably connect to a fluid passageway inlet 116.

In one embodiment, the fluid passageway inlet 116 may connect to the reservoir outlet 114 using a friction fit, an intermediate tube, a male-female connector, or any other method commonly used in the medical or other industry for connecting a tube to a reservoir. Once connected, the reservoir 112 may provide a supply of fluid nutrition that may flow through the fluid passageway 120 and exit from the fluid passageway outlet 132. The rate at which fluid may flow through the fluid passageway 120 may be controlled by the diameter of the fluid passageway outlet 132, a tube clamp (not shown) disposed on any portion of the fluid passageway outlet 132, the elevation of the reservoir 112 relative to the fluid passageway outlet 132, a combination thereof any of the foregoing, or any other means commonly used within the medical industry to control the rate at which fluid flows through a tube. In some embodiments the reservoir 112 and/or the fluid passageway 120 may also include a check valve 108. The check valve 108 may be configured to control the pressure within the reservoir 112 and/or the fluid passageway 120.

The supplemental nutrition apparatus may comprise a support element. A support element as disclosed herein may be configured to engage with, and at least partially surround a user's breast. The support element may comprise a collapsed configuration and an uncollapsed configuration, and may be biased towards the collapsed configuration. In various embodiments, the bias of the support element towards a collapsed configuration allows the support element to lightly clamp the user's breast, thereby securing the support element to the user. In various embodiments, the support element is removably secured to the user. Manipulation of the support element to the uncollapsed configuration may allow easy removal of the support element from the user's breast. In various embodiments, the support element may be deformable, malleable, or sufficiently elastic to retain a bias towards a collapsed configuration after repeated manipulation. With reference to FIGS. 2A-2E, the support element 200 may comprise support frames 202a, 202b having support element clips 204a, 204b, a plurality of fluid passageway support eyelets 206, a support structure 210, and a fluid passageway outlet support 214, according to one embodiment.

The support element 200 may include support frames 202a, 202b, according to some embodiments. The support frames 202a, 202b may be biased to collapse towards each other into a collapsed configuration such that the support element 200 interfaces with users of varying breast size. In various embodiments, the bias of support frames 202a, 202b removably secures the support element 200 to the user's person. In various embodiments, the support frames 202a, 202b utilize springs at the coupling locations 208a, 208b between the support frames 202a, 202b and the support structure 210, wherein the springs may bias the support frames 202a, 202b to rotate inwards and toward the support structure 210. In various embodiments, the support frames 202a, 202b are deformable and/or malleable so as to allow optional and repeatable manipulation into a collapsed configuration or an uncollapsed configuration. In various embodiments, the support frames 202a, 202b are susceptible to elastic deformation. The distal ends 230 of the support frames 202a, 202b may be flexible to better interface with the user's breast.

The support frames 202a, 202b may further include support element clips 204a, 204b. The support element clips 204a, 204b may be configured to interface with a hanging support element (see FIG. 4) to hold the support element 200 in a location proximal to the user's breast.

The support frames 202a, 202b may also include a plurality of fluid passageway support eyelets 206 configured to house portions of the fluid passageway 220. Fluid passageway support eyelets as disclosed herein may be configured to position and engage with one or more portions of the fluid passageway. For example, in various embodiments, fluid passageway support eyelets are configured to guide a portion of the fluid passageway along a side of the user's breast such that it is less visible to a feeding child. In various embodiments, fluid passageway support eyelets are configured to manage excess lengths of the fluid passageway such that it is removed from the view and/or grasp of a feeding child.

The support element 200 may include the support structure 210, according to some embodiments. The support structure 210 may be operably connected to the support frames 202a, 202b at coupling locations 208a, 208b. In some embodiments, the support structure 210 may be operably connected to a sliding mechanism 218. The sliding mechanism 218 may be configured to permit lateral telescopic movement of the support structure 210. In various embodiments, lateral telescopic movement of the support structure 210 enables support element 200 to be affixed securely to breasts of various sizes and/or shapes. In one embodiment, the support structure 210 is partially hollow to accommodate housing a portion of the sliding mechanism 218 within the support structure 210.

The support element 200 may include the fluid passageway outlet support 214, according to some embodiments. A fluid passageway outlet support as described herein may be configured to position the fluid passageway relative to the user's breast. In various embodiments, the fluid passageway outlet support is configured to position the fluid passageway outlined proximate to the user's nipple and/or at the user's areola. The fluid passageway outlet support may extend from a portion of the support element (for example, a support frame or the support structure) towards the center of the support element or, when in use, towards the user's nipple. However, the fluid passageway outlet support may comprise any size and/or shape suitable for positioning the fluid passageway outlet proximate to the user's nipple and/or at the user's areola.

Figure 2A:
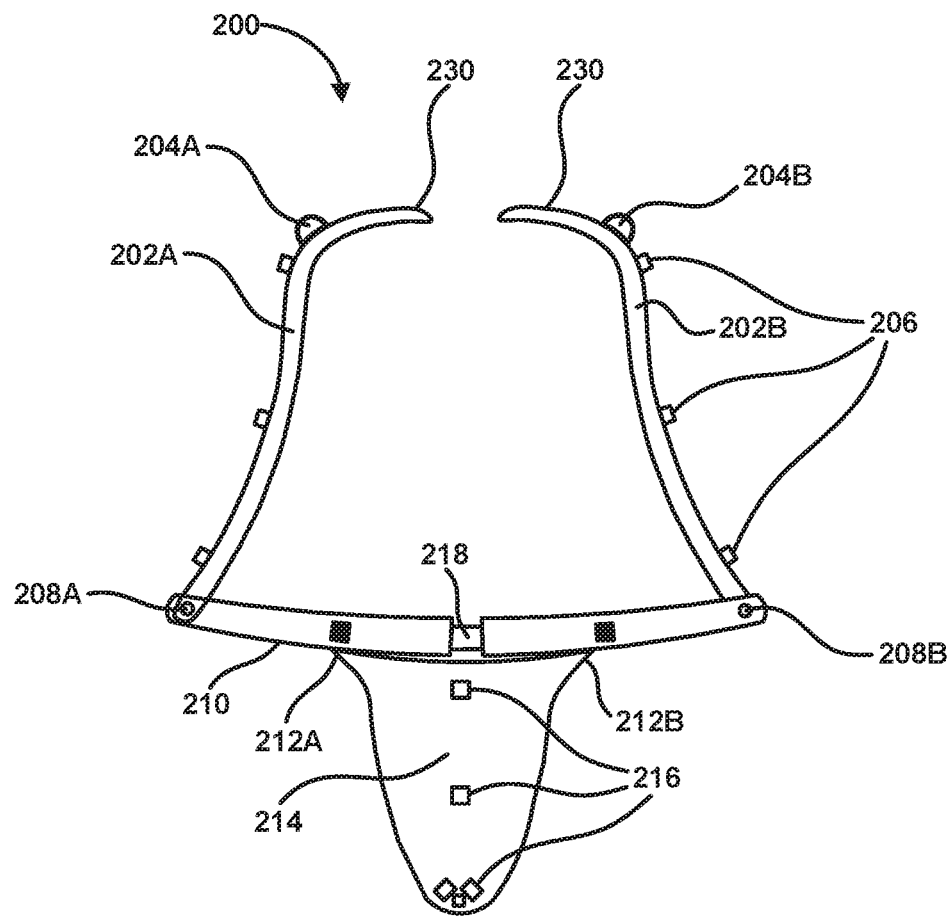
Figure 2B:
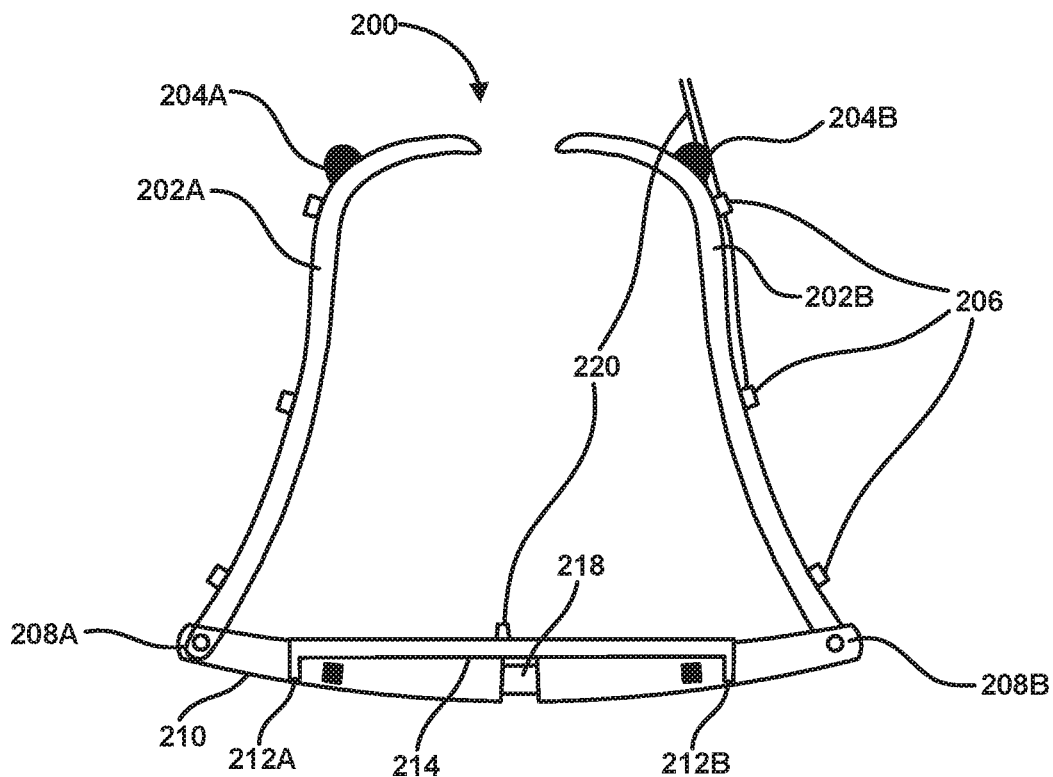
Figure 2C:
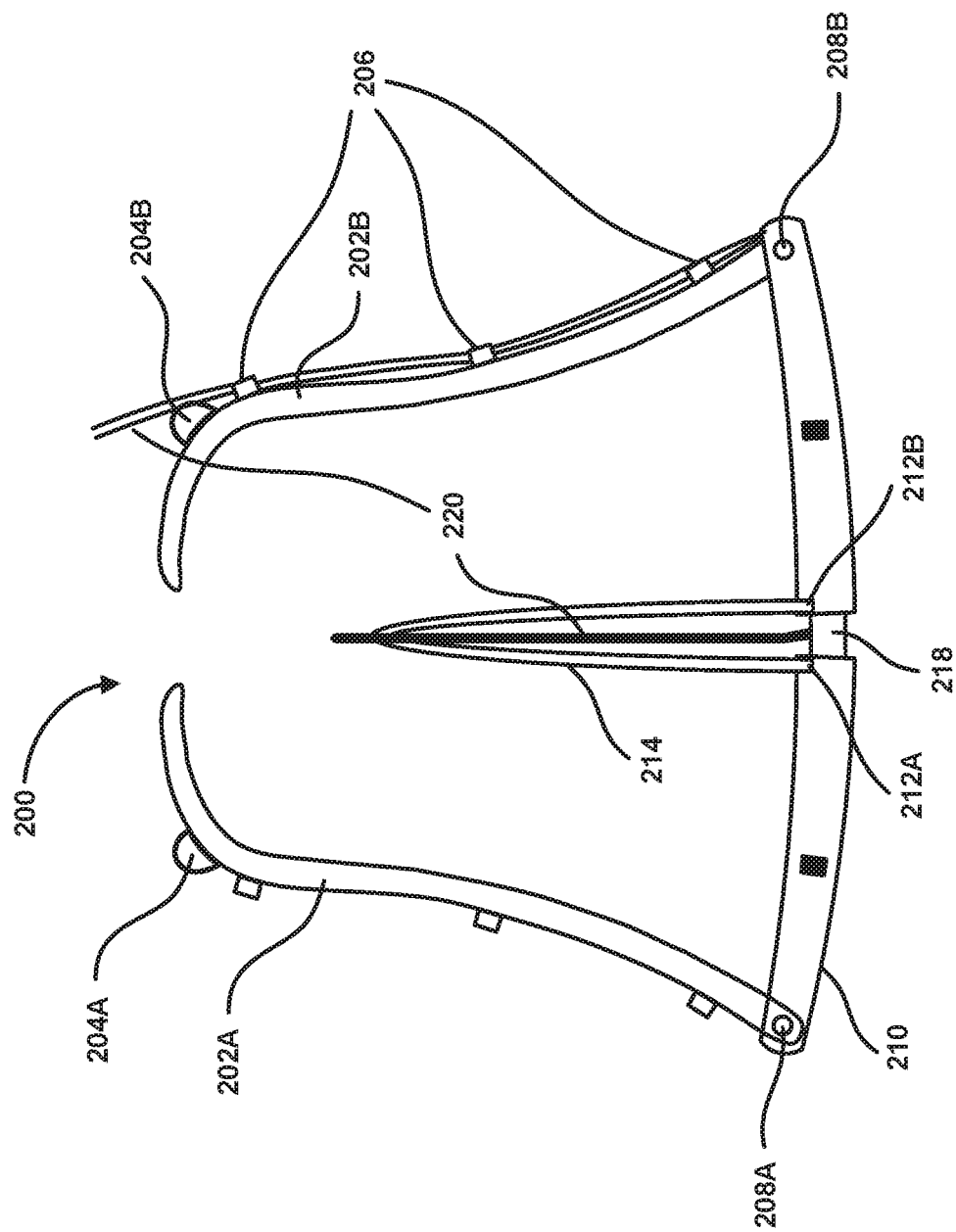
Figure 2D:
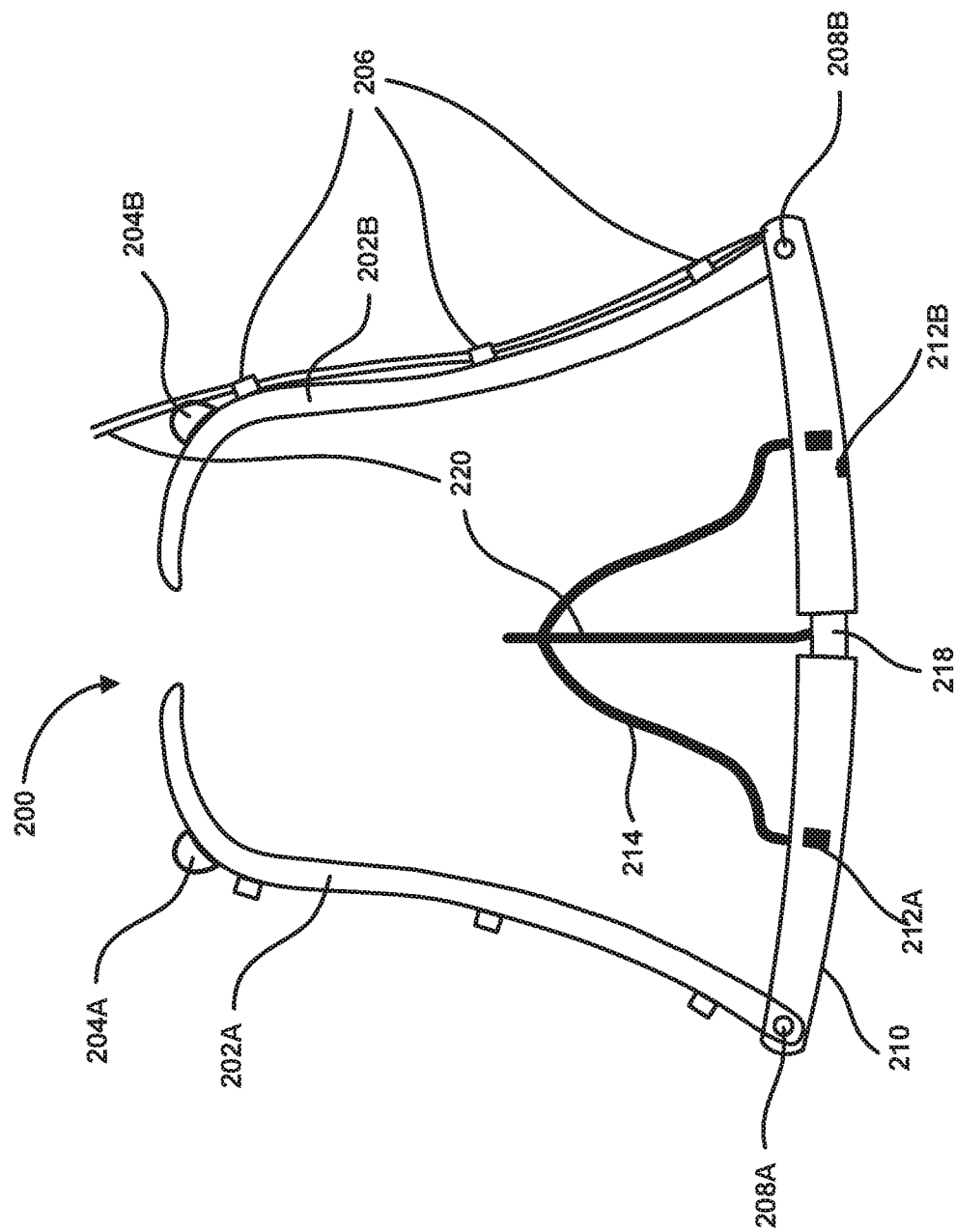
Figure 2F:
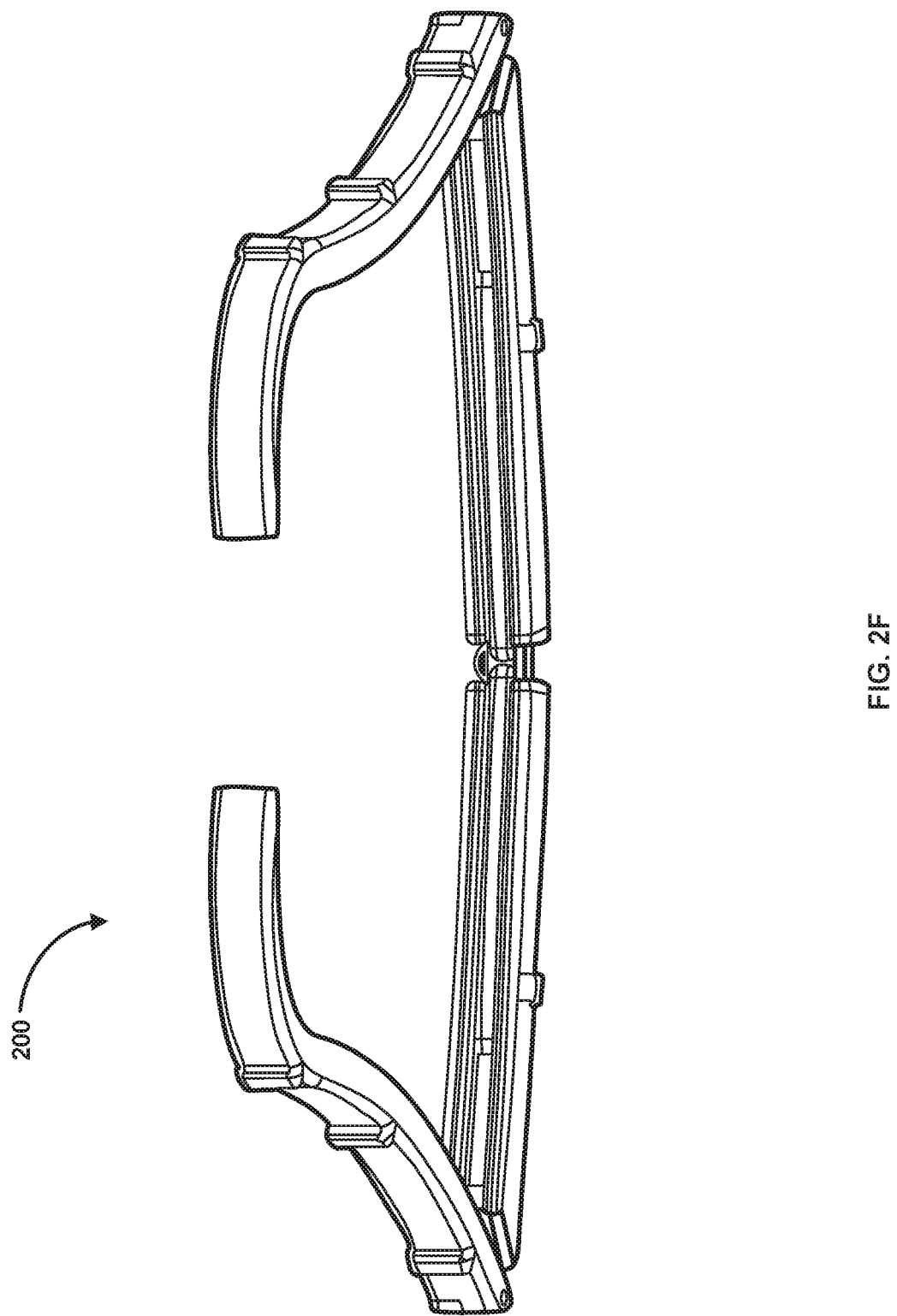
Figure 2G:
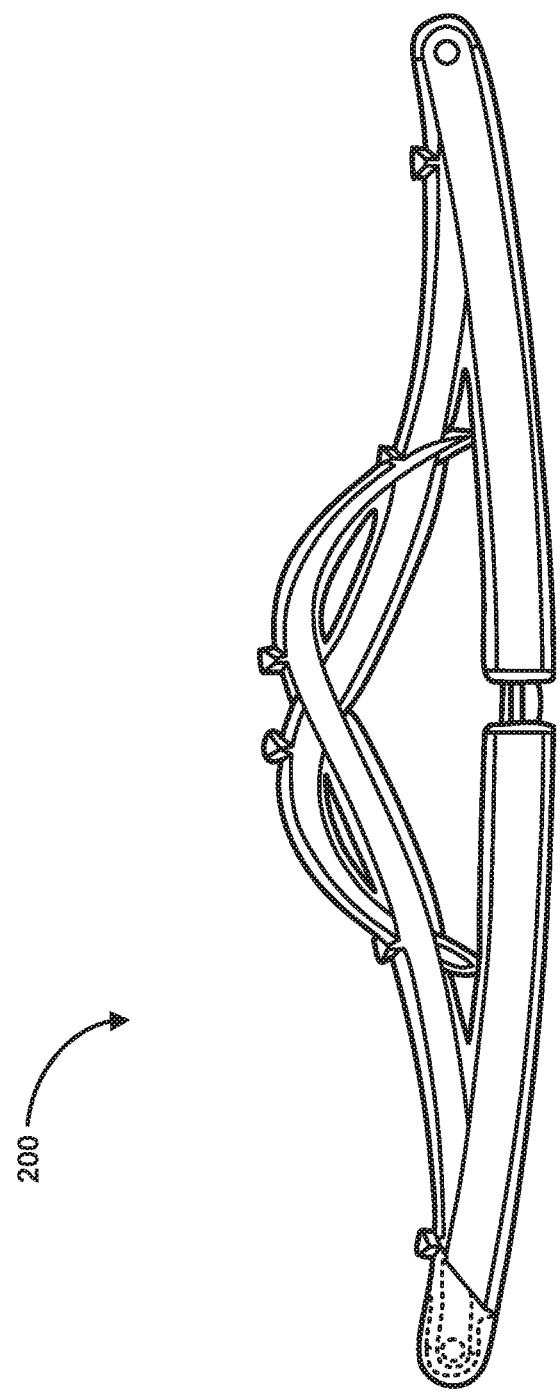

In some embodiments, the fluid passageway outlet support 214 may comprise a wire-shaped or elongated member that attaches to support structure 210 at a first end 212A and a second end 212B. First end 212A and second end 212B may be attached at various points along support structure 210 so as to adjust the length and/or distance away from support structure 210 that fluid passageway outlet support 214 extends. The fluid passageway outlet support 214 may utilize a plurality of clips 216 to position and hold the fluid passageway 220 in place while the supplemental nutrition apparatus is being used. In some embodiments, the fluid passageway outlet support 214 may be configured to collapse or otherwise fold into the support structure 210 (for example, completely housed with the support structure 210) (See FIGS. 2F and 2G). The fluid passageway outlet support 214 may also be configured to extend from the support structure 210 to various lengths in order to accommodate for varying positions of the user's nipple relative to the support structure 210.

In various embodiments, the supplemental nutrition apparatus further comprises a reservoir system. As described herein, the reservoir system may be configured to retain and communicate a volume of liquid to the fluid passageway under a user's direction and control. The reservoir system may be reusable or one-time use. The reservoir system may comprise mechanisms for attachment to a user of the supplemental nutrition apparatus and/or to other object. The reservoir system may comprise apparatus for controlling the rate of fluid flow to and/or through the fluid passageway, for example, a valve, clamp, gate, regulator, or the like. The reservoir system may comprise a filter configured to separate solids from fluid nutrition communicated into the fluid passageway, so as to prevent clogging, plugging, or other obstruction of fluid flow through the fluid passageway.

Figure 3A:
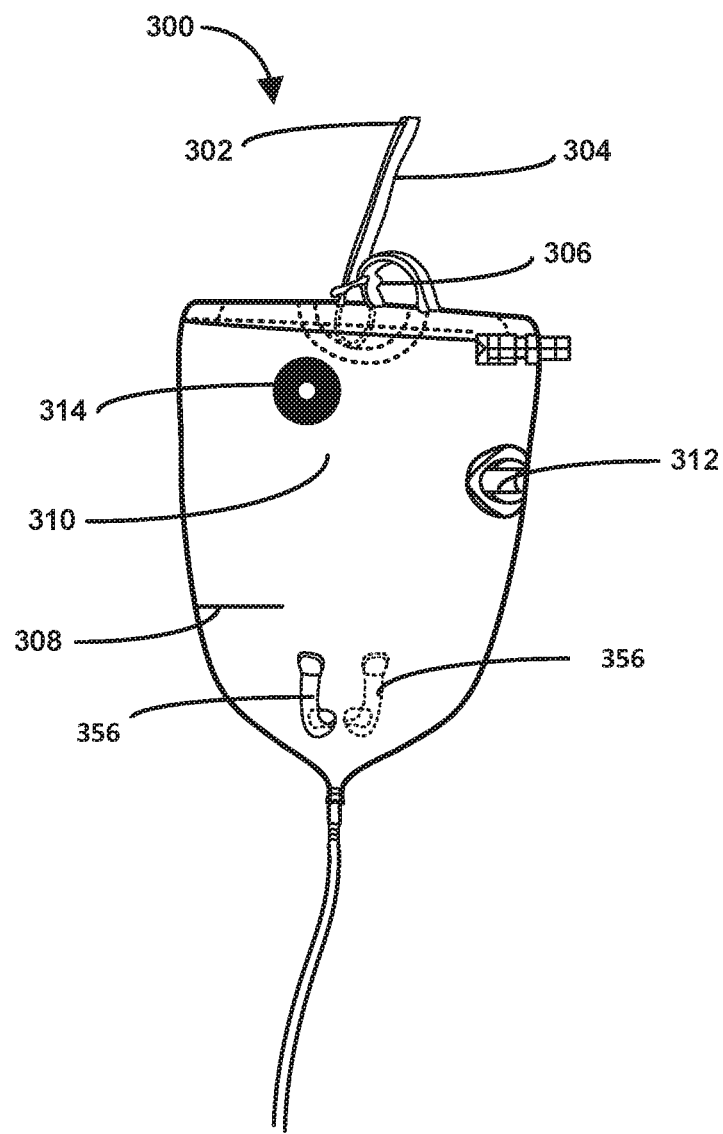
FIG. 3A illustrates a perspective view of portions of a supplemental nutrition apparatus, in accordance with various embodiments.

FIG. 3A illustrates an embodiment of a reservoir system 300 of a supplemental nutrition apparatus. The reservoir system 300 illustrated in FIG. 3A may comprise an attachment element 302, a support strap 304, an adjuster 306, an access point 308, a reservoir 310, a reservoir mounting element 312, a check valve 314, and at least one reservoir clip 356, according to one embodiment.

The attachment element 302 may be configured to secure the reservoir 310 in an elevated position relative to the fluid passageway outlet. The attachment element 302 may be coupled to reservoir 310. In various embodiments, attachment element 302 is disposed at or near the top of reservoir 310. However, attachment element 302 may be disposed on any portion of reservoir system 300 suitable for use in an nutritional supply apparatus. In some embodiments, the attachment element 302 may comprise a clip that attaches to the user's garments (for example, a brassiere strap). In another embodiment, the attachment element 302 may be a pin or clamp that attaches to the user's garment to secure the reservoir 310 in an elevated position. The position of the reservoir 310 may be adjusted by manipulating the length of the support strap 304. In some embodiments, an adjuster 306 may be used to adjust the length of the support strap 304. For example, the adjuster 306 may comprise a set of rings and/or a slide used to adjust the length of the support strap 304 to effectively elevate or lower the reservoir 310.

Figure 3B:
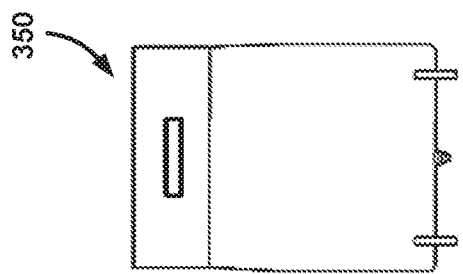
FIGS. 3B-3G illustrates various views of a reservoir, in accordance with various embodiments.
Figure 3C:
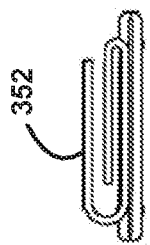
Figure 3D:
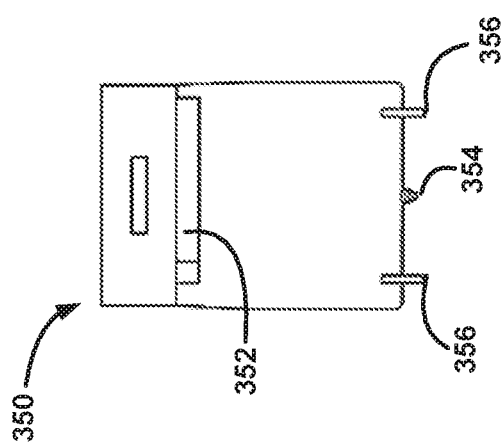
Figure 3E:
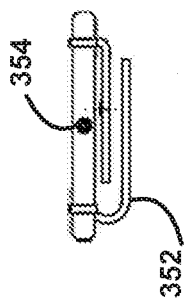
Figure 3F:
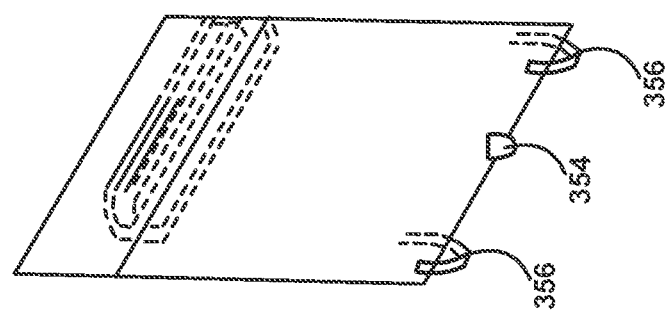
Figure 3G:
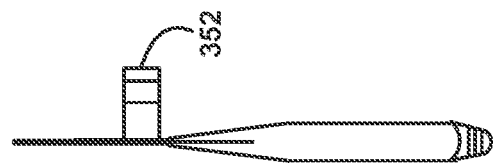

The reservoir system 300 may also include an access point 308. The access point 308 may be configured to allow a user to insert or fill the reservoir 310 with fluid before and/or after each use. For example, the access point 308 may be a compression seal, slide-lock opening, zippered opening, adhesive seal, or any other suitable mechanism for optionally opening the reservoir 310 and accessing an interior thereof. As another example, the access point 308 may comprise a cap system utilizing threads or a friction fit to secure the cap to the reservoir 310. The access point 308 may comprise any method or system known in the art that allows a user to insert and retain fluid within the reservoir 310. In various embodiments, the access point is disposed at the top of the reservoir. However, the access point may be disposed on any suitable portion of the reservoir. In various embodiments, reservoir system 300 further comprises a filter disposed between access point 308 and a fluid outlet 354 (with momentary reference to FIGS. 3B and 3D). Reservoir system 300 may be configured to receive fluid nutrition through access point 308, to communicate fluid nutrition through and/or across the filter, and to pass the filtered fluid nutrition to and through fluid outlet 354 into the fluid passageway.

In some embodiments, the reservoir system 300 may also include a reservoir mounting element 312. The reservoir mounting element 312 may be configured to secure the reservoir 310 to the user while using the supplemental nutrition apparatus. The reservoir mounting element 312 may be co-molded into the reservoir 310 during manufacturing or attached as a separate component using adhesive or any other suitable method of attachment to the reservoir. In some embodiments, the reservoir mounting element 312 is located on the back of the reservoir 310 (i.e., close to the user). In other embodiments, the reservoir mounting element 312 may be positioned on the top, bottom, and/or side of the reservoir 310. In yet other embodiments, the supplemental nutrition apparatus may utilize a plurality of reservoir mounting elements 312 to secure the reservoir 310. The reservoir mounting element 312 may be a clip, clamp, pin, combination thereof, or any other method known to one having skill in the art to secure a reservoir in a fixed position.

In various embodiments, and with reference to FIGS. 3B-3G, a reservoir 350 (as has already been described herein) comprises a reservoir mounting element 352 (as has already been described herein), a fluid outlet 354, and one or more guide hooks 356. Fluid outlet 354 may be configured to couple to fluid passageway such that the interior of reservoir 350 is in fluid communication with the interior of the fluid passageway. Guide hooks 356 may be disposed on any suitable portion of reservoir 350 and may be configured to receive a portion of the fluid passageway. In various embodiments, excess length of fluid passageway may be managed and removed from the view and/or grasp of a feeding child when disposed on or in guide hooks 356. Guide hooks may be configured to couple with a hanging support element (see FIG. 4) to hold the support element in a location proximal to the user's breast.

Figure 4:
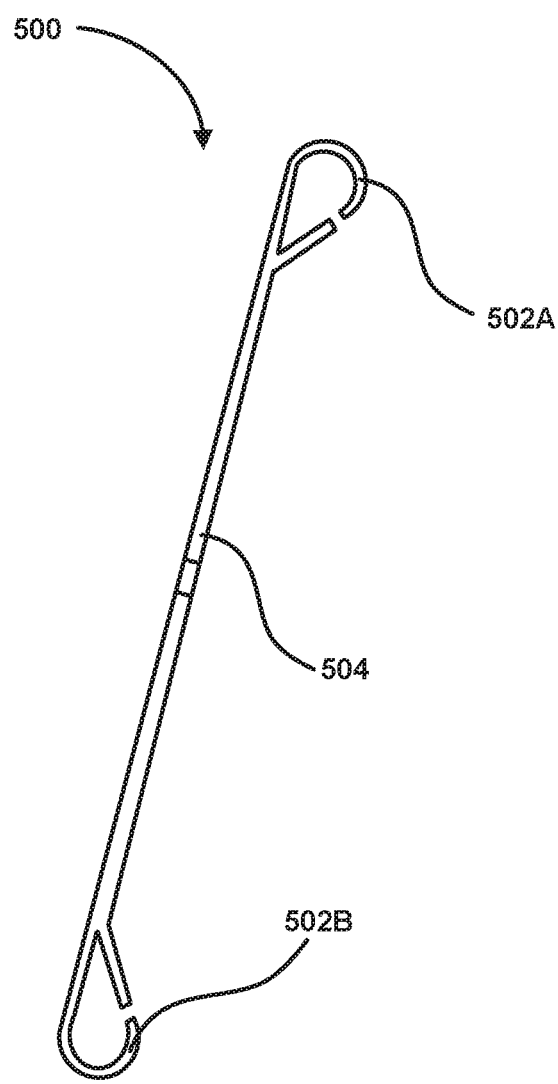
FIG. 4 illustrates a perspective view of a hanging support element, in accordance with various embodiments.

FIG. 4 illustrates an embodiment of a hanging support element 500 of the supplemental nutrition apparatus for fluid delivery and lactation stimulation. In some embodiments, the hanging support element 500 may include a first looped end 502a and a second looped end 502b connected at a midpoint 504. In some embodiments, the first looped end 502a and the second looped end 502b may be operably coupled to at least one reservoir clip and at least one support element clip to fix the support element proximate to the user's person.

Figure 5A:
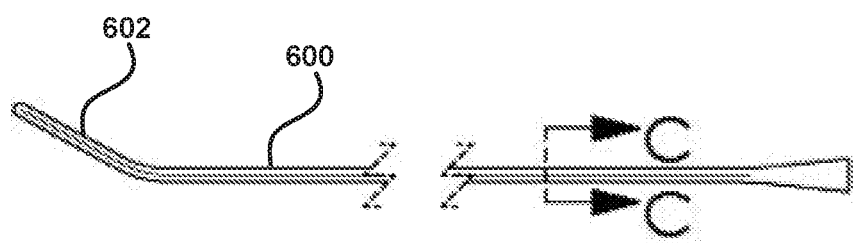
FIG. 5A illustrates a broken side view of a fluid passageway, in accordance with various embodiments.
Figure 5B:
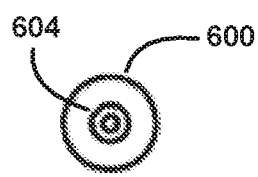
FIG. 5B illustrates a cross-section view of the C-C cross-section of FIG. 5A, in accordance with various embodiments.
Figure 7:
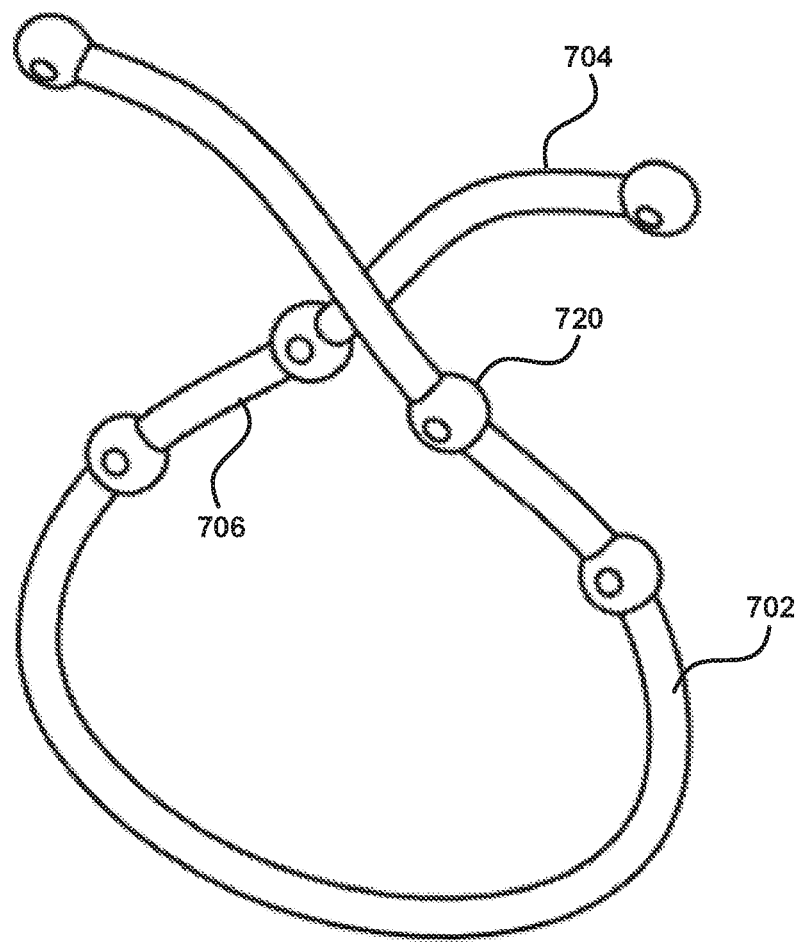
FIG. 7 illustrates a perspective view of a portion of a support element, in accordance with various embodiments.

The fluid passageway as described herein may comprise a capillary tube disposed and extending between a reservoir and a support element. However, in various embodiments, the fluid passageway can comprise a pipe, hose, duct, channel, or any other suitable conduit for communicating fluid from the reservoir proximate to the user's nipple. With reference now to FIGS. 5A and 5B, fluid passageway 600 may comprise a capillary tube having a lumen 604 through which fluid may be communicated. Lumen 604 may comprise an interior diameter of between about 0.05 mm to about 2.5 mm. In various embodiments, lumen 604 comprises an interior diameter of between about 0.05 mm to about 0.5 mm. In various embodiments, lumen 604 comprises an interior diameter of about 0.07 mm. However, the lumen may comprise any interior diameter suitable for communication of supplemental nutrition fluid to a feeding child.

In various embodiments, fluid passageway 600 comprises an exterior diameter of between about 0.1 mm and about 2.7 mm. In various embodiments, fluid passageway 600 comprises an exterior diameter of between about 0.5 mm and about 0.6 mm. In various embodiments, fluid passageway 600 comprises an exterior diameter of about 0.17 mm. However, the fluid passageway may comprise any exterior diameter suitable to allow a child to take a portion of the fluid passageway into his/her mouth without distraction or disruption of feeding.

In various embodiments, fluid passageway 600 comprises a distal end 602 disposed distally from the reservoir. Distal end 602 may comprise a greater interior diameter than proximally-located portions of fluid passageway 600. Distal end 602 may comprise a greater exterior diameter than proximally-located portions of fluid passageway 600. Stated differently, distal end 602 may be flared to facilitate communication of fluid into a feeding child's mouth. In various embodiments, distal end 602 may comprise a longitudinal axis that is non-parallel to a longitudinal access of proximal portions of fluid passageway 600. Stated differently, fluid passageway 600 may be bent and/or angled. A bent and/or angled distal end 602 may facilitate latching of a child on a nipple that is inverted or small.

In various embodiments, and with reference to FIGS. 6A-9, a support element 700 may comprise a unitary support frame 702. Unitary support frame 702 may function in a manner as described with respect to support frame 202A, 202B and/or support structure 210 as has already been described. A unitary support frame may comprise a generally "u"-shaped member with one arm extending generally upwardly from each end of a generally curved midportion. In various embodiments, unitary support frame 702 is biased towards a collapsed configuration in which distal ends 704 extend toward and/or partially across a midline of the unitary support frame 702 as can be seen in FIGS. 6A-8. Bias towards the collapsed configuration may facilitate compression of the unitary support frame on a user's breast.

In various embodiments, the upwardly extending arms of unitary support frame 702 may be bent such that distal ends 704 extend back towards the user when in use. Bending of distal ends 704 may increase the contact area between the user and unitary support frame 702, thereby facilitating the securing of unitary support frame 702 to a user's breast. Similarly, the generally curved midportion may increase the contact area between the user and unitary support frame 702, thereby facilitating the securing of unitary support frame 702 to a user's breast. In various embodiments, the generally curved midportion may improve the durability of the unitary support frame and/or prevent structural damage to the unitary support frame when the upwardly extending arms are pulled outward, away from one another.

Unitary support frame 702 may comprise a deformable and/or malleable material such that a user may size, configure, and/or deform unitary support frame 702 so as to be securely affixed to a user's unique breast size and/or shape. In various embodiments, unitary support frame 702 comprises a material capable of repeated elastic deformation from the collapsed state to the uncollapsed state. In various embodiments, unitary support frame 702 comprises a medial bend 706 disposed proximally to each distal end 704 such that a medial bend 706 will be positioned on the lateral sides of a user's breast during use of the supplemental nutrition apparatus. Medial bends 706 may be configured to press inwardly against a user's breast so as to better secure the unitary support frame 702 to the user.

The unitary support frame comprises one or more fluid passageway support eyelets, as already described herein. In various embodiments, fluid passageway support eyelets 710 are proud relative to unitary support frame 702 and define an aperture whose central axis is disposed generally parallel to the longitudinal axis of unitary support frame 702. In various embodiments, fluid passageway support eyelets 720 are disposed in line with unitary support frame 702 and define an aperture whose central axis is disposed generally perpendicular to the longitudinal axis of unitary support frame 702.

Figure 8:
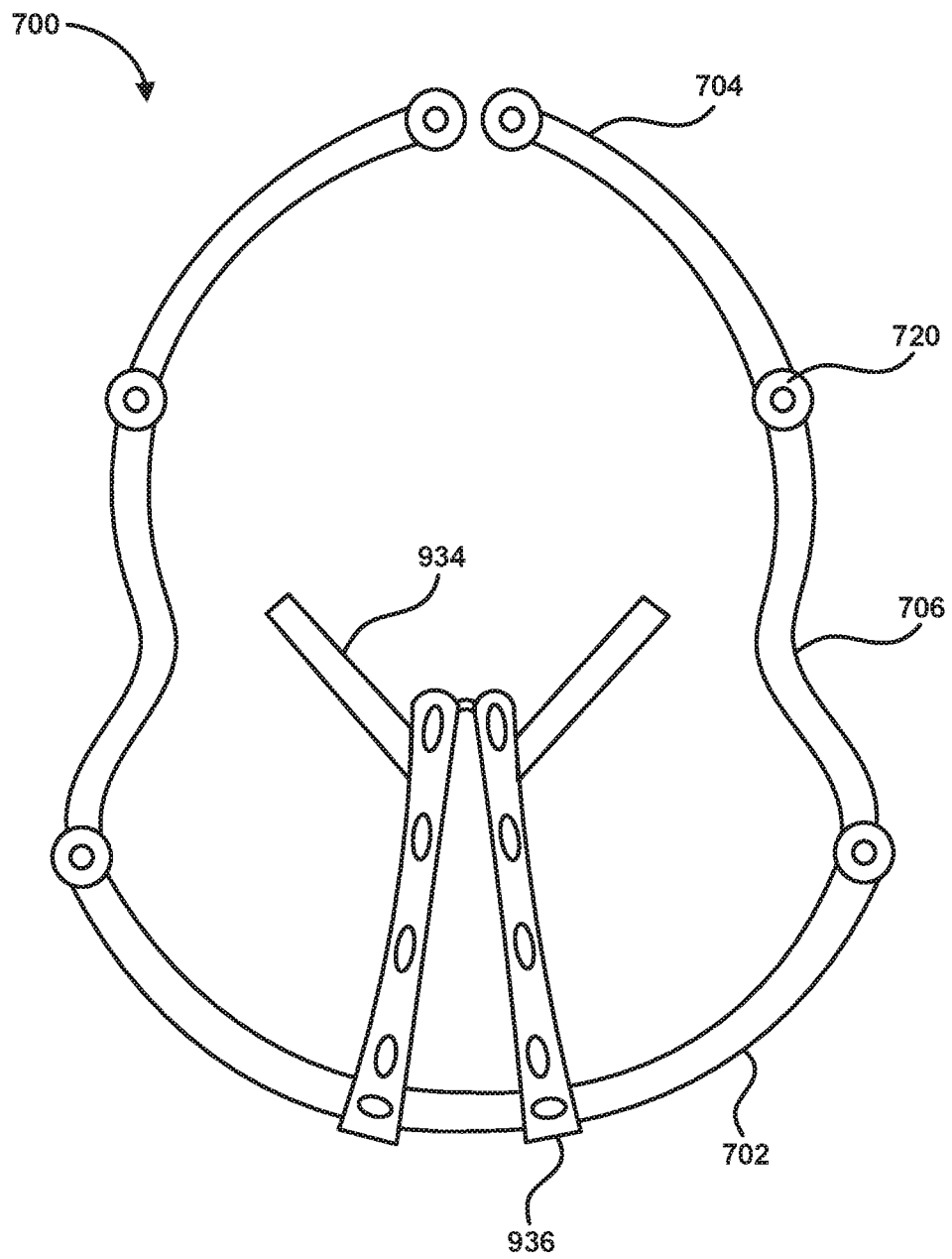
FIG. 8 illustrates a perspective view of a support element, in accordance with various embodiments.
Figure 9:
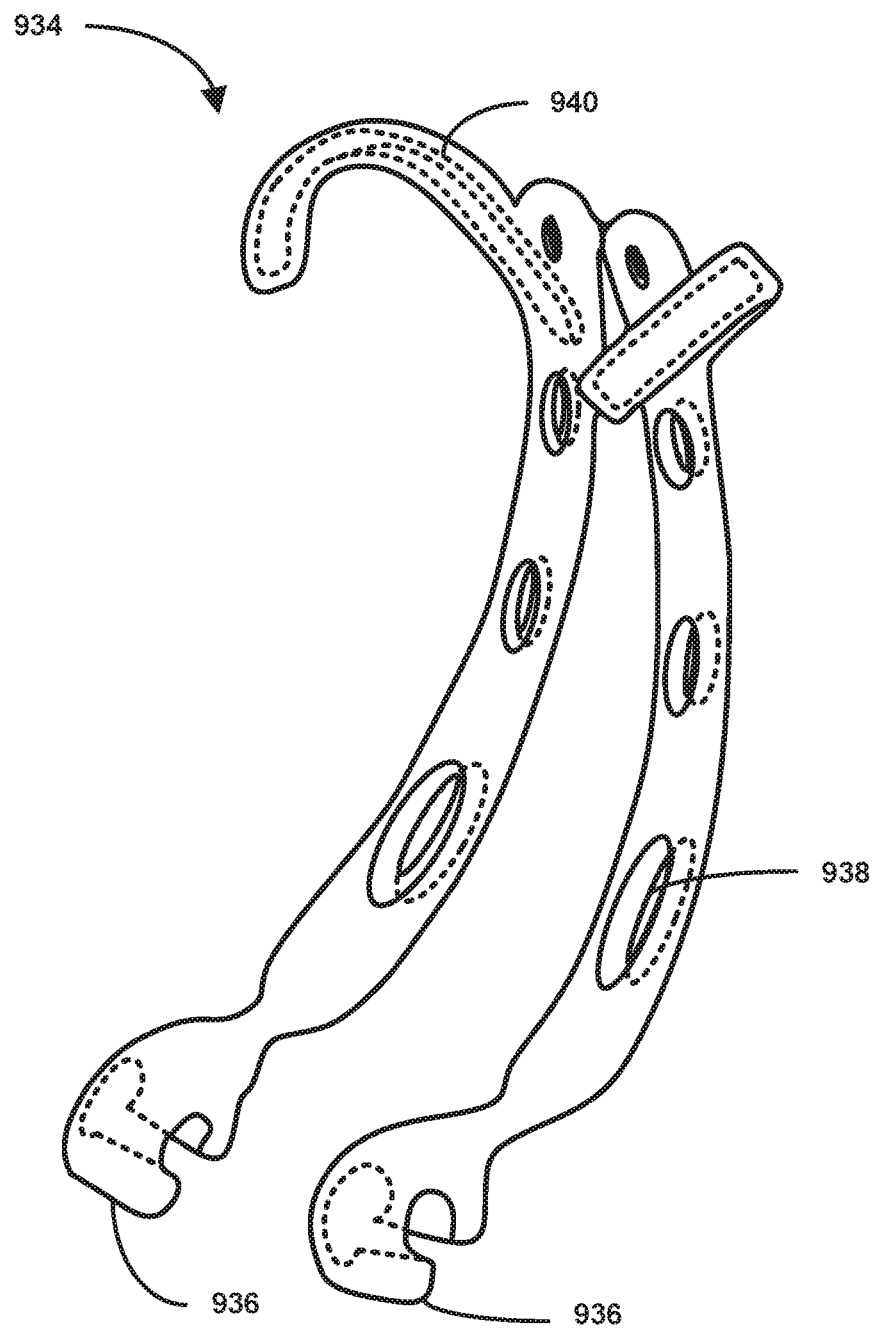
FIG. 9 illustrates a perspective view of a fluid passageway outlet support, in accordance with various embodiments.
Figure 10:
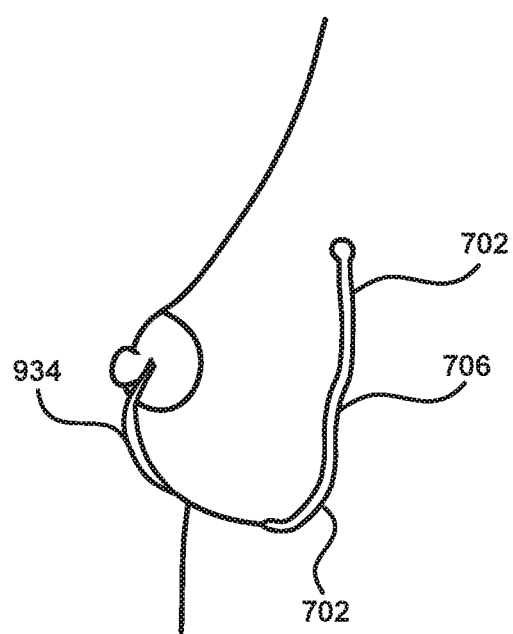
FIG. 10 illustrates a perspective view of a support element, in accordance with various embodiments.

In various embodiments, and with reference to FIGS. 8-10, support element 700 may comprise a fluid passageway outlet support 934 as already described herein. Fluid passageway outlet support 934 may be coupled to unitary support frame 702 via one or more attachment points 936. An attachment point 936 may comprise clips, clasps, snaps, loops, hooks, or the like. In various embodiments, attachment point 936 is configured to allow fluid passageway outlet support 934 to rotate about the longitudinal axis of unitary support frame 702. In various embodiments, rotation of fluid passageway outlet support 934 allows support element 700 to be configured for use with breasts of various shapes and sizes, including breasts with mild to severe ptosis.

Fluid passageway outlet support 934 may comprise one or more guide apertures 938 extending between attachment point 936 and nipple cradle 940. The guide apertures 938 may be configured to receive, position, and/or manage a fluid passageway as already described herein. The nipple cradle 940 may comprise a portion of fluid passageway outlet support 934 configured to be disposed proximal to a user's nipple and/or at a user's areola during use of the nutritional support apparatus.

Figure 11:
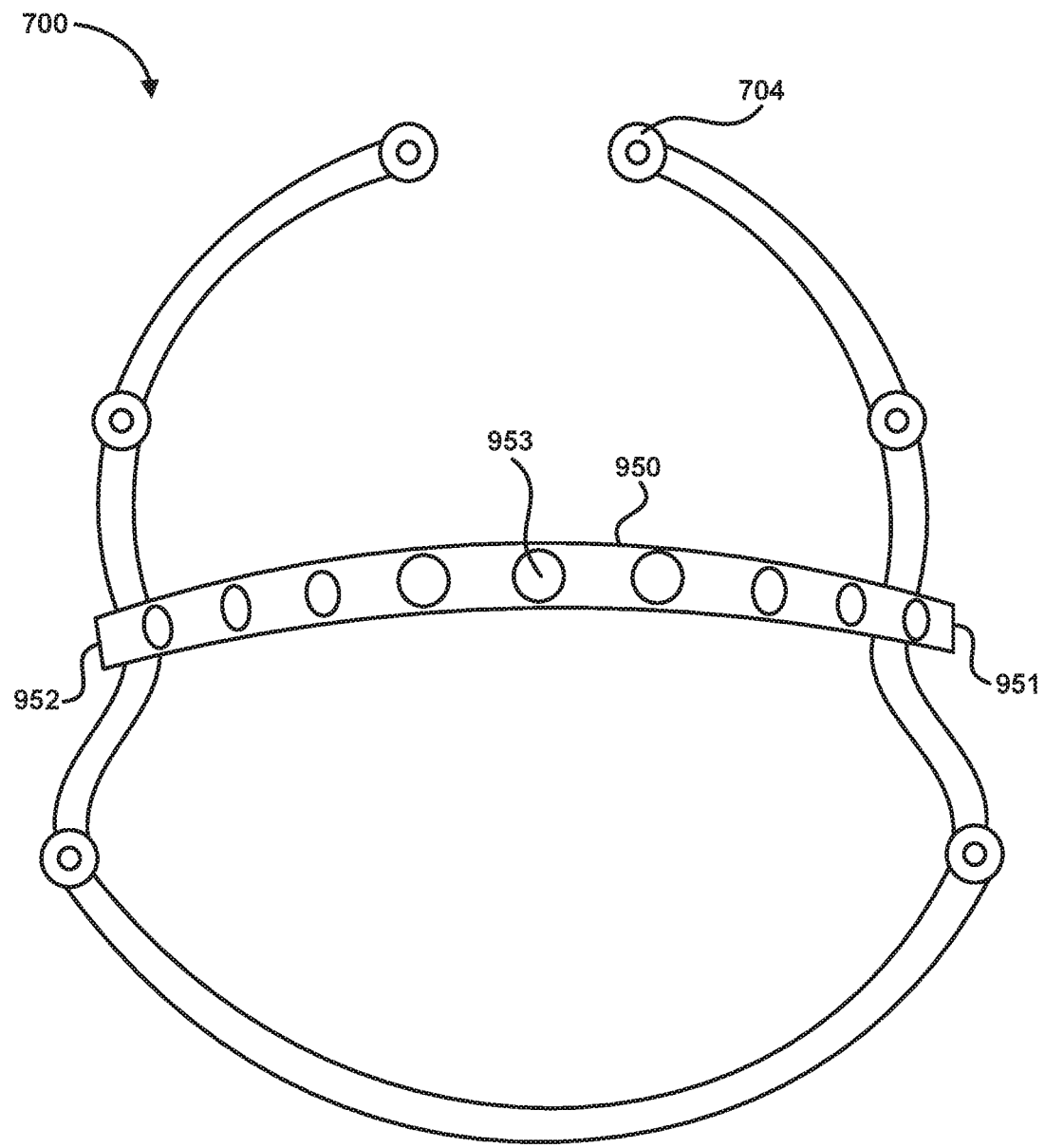
FIG. 11 illustrates a perspective view of a support element, in accordance with various embodiments.
Figure 12A:
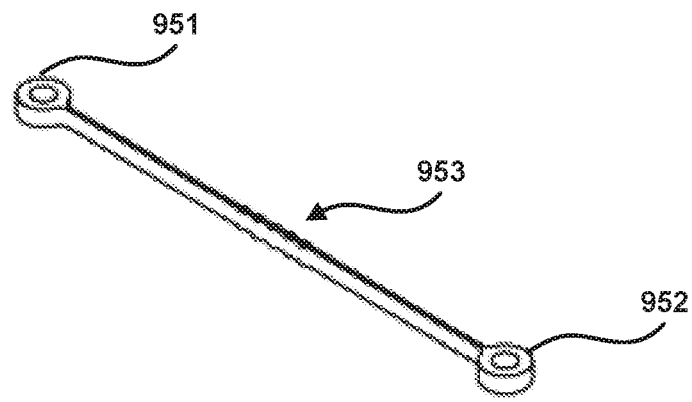
FIGS. 12A-12B illustrate various views of a support element belt, in accordance with various embodiments.
Figure 12B:
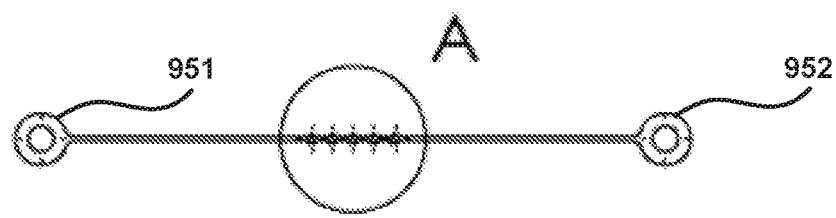
Figure 12C:
FIG. 12C illustrates a detail view of area A of FIG. 12B, in accordance with various embodiments.

With reference now to FIGS. 11-12C, a support element 700 may comprise a support element belt 950 coupled to a unitary support frame 702. Support element belt 950 may be configured to extend from a first lateral side of unitary support frame 702 to a second lateral side of unitary support frame 702, such that support element belt 950 is configured to cross generally over the midline of a user's breast and proximal to the user's nipple during use of the supplemental nutrition apparatus.

Support element belt 950 may comprise a first belt attachment 951, a second belt attachment 952, and an elongated central portion disposed therebetween. First belt attachment 951 and second belt attachment 952 may comprise loops and/or may define apertures through which the distal ends 704 of unitary support frame 702 may be threaded. In various embodiments, support element belt 950 may be translated up or down along unitary support frame 702 so as to optimally position support element belt 950 for an individual user. In various embodiments, first belt attachment 951 and second belt attachment 952 may comprise hooks, clasps, snaps, or any other suitable mechanism for adjustably coupling support element belt 950 to unitary support frame 702. In various embodiments, first belt attachment 951 and second belt attachment 952 are configured to allow pivoting rotation of support element belt 950 relative to unitary support frame 702 so as to optimally position support element belt 950 for an individual user.

In various embodiments, support element belt 950 comprises one or more fluid passageway fasteners 953 disposed in and/or defined by the elongated central portion. The fluid passageway fastener 953 is configured to receive, position, and/or guide the fluid passageway outlet proximate to the user's nipple and/or at the user's areola. In various embodiments, fluid passageway fastener 953 comprises an aperture defined by the elongated central portion. However, fluid passageway fastener 953 may comprise a clip, clasp, snap, or any other fastener suitable for coupling the fluid passageway to the elongated central portion.

Figure 13A:
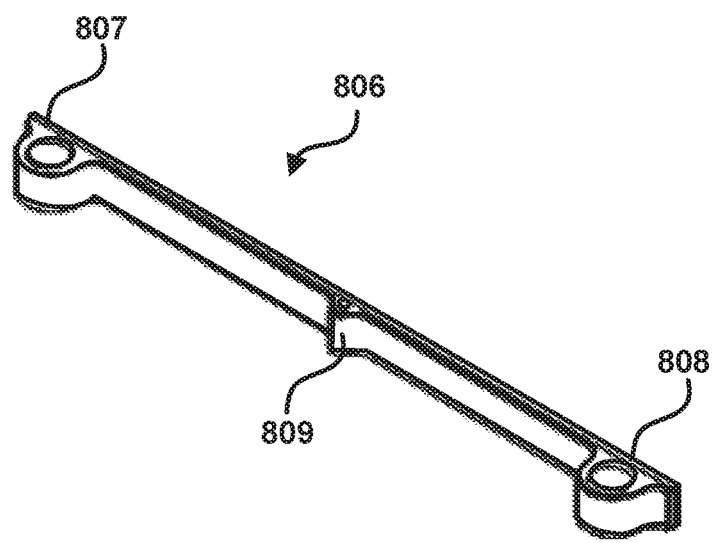
FIGS. 13A-13B illustrate various views of a support element belt, in accordance with various embodiments.
Figure 13B:
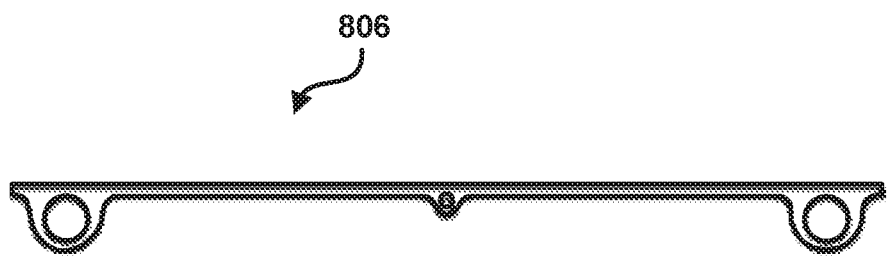
Figure 14:
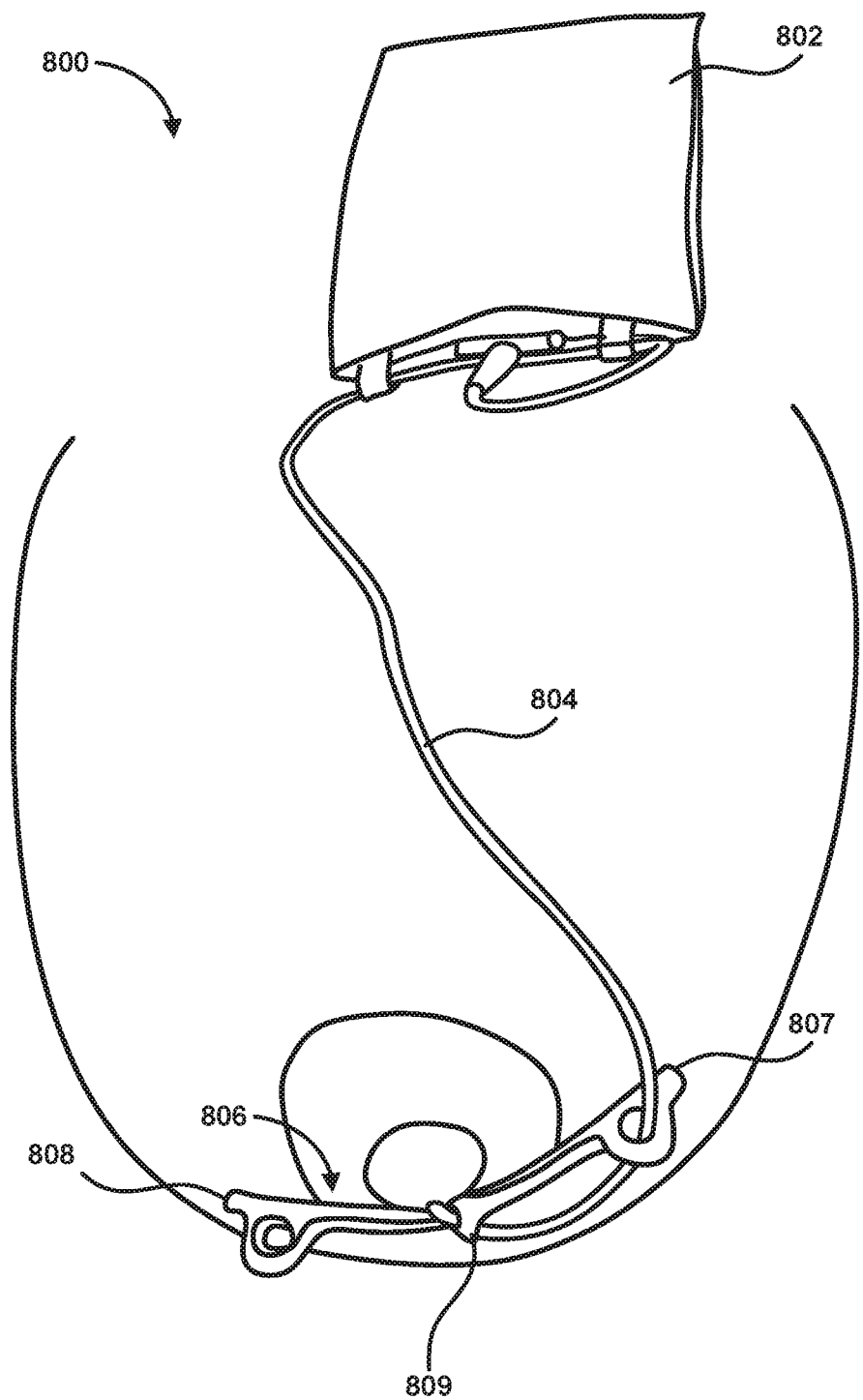
FIG. 14 illustrates a perspective view of a supplemental nutrition apparatus, in accordance with various embodiments.

In various embodiments, and with reference now to FIGS. 13A-14, a supplemental nutrition apparatus 800 may comprise a reservoir 802, a fluid passageway 804, and a support element belt 806. Support element belt 806 may comprise a first belt attachment 807, a second belt attachment 808, and an elongated central portion extending therebetween. First belt attachment 807 and second belt attachment 808 may comprise loops and/or may define apertures through which fluid passageway may be received, positioned, and/or guided. In various embodiments, such loops and/or apertures, as well as guide hooks, guide apertures, support elements clips, fluid passageway support eyelets as have been described herein, are configured to do one or more of the following: minimize the occurrence of kinks in the fluid passageway, remove the fluid passageway from the view of a child using the supplemental nutrition apparatus, minimize the occurrence of a child grabbing, pulling, and/or being distracted by the present of the fluid passageway, and/or other benefits as described herein. First belt attachment 807 and second belt attachment 808 may be disposed proud relative to the elongated central portion and may define a central axis generally perpendicular to the longitudinal axis of support element belt 806.

Adhesive may be disposed on a back side (i.e., the side that abuts the user's body during use) of first belt attachment 807 and second belt attachment 808 such that support element belt 806 may be secured to a user's breast without use of a unitary support frame or other apparatus. In various embodiments, adhesive is not disposed on the back side of the elongated central portion. Omitting adhesive from the elongated central portion and/or restricting adhesive to the first belt attachment and the second belt attachment may prevent a child from ingesting or otherwise receiving adhesive in his/her mouth during feeding.

Support element belt 806 may comprise one or more fluid passageway fasteners 809 disposed in and/or defined by the elongated central portion. The fluid passageway fastener 809 is configured to receive, position, and/or guide the fluid passageway outlet proximate to the user's nipple and/or at the user's areola. In various embodiments, fluid passageway fastener 809 comprises an aperture defined by the elongated central portion. However, fluid passageway fastener 809 may comprise a clip, clasp, snap, or any other fastener suitable for coupling the fluid passageway to the elongated central portion.

A support element belt as described herein may comprise any length suitable to be disposed on a user's breast such that the first belt attachment and the second belt attachment are disposed sufficiently far from the areola so as to not be brought into the child's mouth during feeding. The support element belt may comprise any length suitable to be disposed on a user's breast such that fluid passageway fastener is disposed sufficiently close to the user's nipple so as to be brought into the child's mouth during feeding. The support element belt may be disposed on, and/or adhered to, a user's breast at any location suitable to dispose a fluid passageway of a supplemental nutrition apparatus proximate to a user's nipple. In various embodiments, optional adhesion of the support element belt to various portions of a user's breast allows the supplemental nutrition apparatus to be used with breasts of various shapes and sizes, including breasts with mild to severe ptosis.

In various embodiments, a supplemental nutrition apparatus comprising a unitary support frame and/or a support element belt as described herein may be configured for use without additional breastfeeding garments or devices. Portions of such a supplemental nutrition apparatus may be configured to be worn under a user's clothes for extended durations such as 1 hour, 4 hours, 8 hours, 12 hours, or more.

Portions of the supplemental nutrition apparatus disclosed herein may be made of various materials. For example, portions of the supplemental nutrition apparatus that are configured to be in contact with nutritional fluid and/or a child's mouth, such as the reservoir, the fluid passageway, the fluid passageway outlet support, and/or the support element belt, comprise food-grade, BPA-free materials. In various embodiments, portions of the supplemental nutrition apparatus that are configured to be in contact with the child's mouth are thin and/or low-profile relative to the surface of the user's breast. Low profile components decrease and/or mitigate interference of the normal feeding process by the supplemental nutrition apparatus. In various embodiments, portions of the supplemental nutrition apparatus that are configured to be in contact with nutritional fluid and/or a child's mouth comprise silicon. However, in various embodiments, portions of the supplemental nutrition apparatus comprise any suitable material.

In various embodiments, portions of the supplemental nutrition apparatus disclosed herein may comprise a structural core and an overmold. For example, any one or more of a support element, support frame, support structure, unitary support frame, fluid passageway outlet support, support element belt, or any other suitable portion of the supplemental nutrition apparatus may comprise a structural core and an overmold. The structural core may comprise a deformable material. The structural core may comprise a material having elastic properties such that it may be deformed temporarily and may return to its original shape. The overmold may comprise a material that is softer than the structural core so as to improve the comfort of the supplemental nutrition apparatus on a user's body. The overmold may comprise a material that is softer than the structural core so as to reduce chafing, rubbing, pinching, scratching, and/or the like between portions of the supplemental nutrition apparatus and the user. The overmold may comprise a material that is softer than the structural core so as to improve surface friction between portions of the supplemental nutrition apparatus and the user's body, thereby securing the supplemental nutrition apparatus on the user's body. In various embodiments, the overmold comprises a smooth texture. In various embodiments, the overmold comprises a texture having ridges, bumps, divots, creases, protrusions, or an otherwise rough or course texture so as to improve surface friction between portions of the supplemental nutrition apparatus and the user's body, thereby securing the supplemental nutrition apparatus on the user's body.

The various portions of a supplemental nutrition apparatus may be used only one time. For example, the reservoir and/or fluid passageway may be configured for one-time use. In various embodiments, various portions of a supplemental nutrition apparatus are manufactured to prevent multiple uses. In other embodiments, some or all parts of a supplemental nutrition apparatus may be reusable.

In various embodiments, one or more portions of a supplemental nutrition apparatus may comprise a clear, transparent, and/or semi-transparent material. In various embodiments, one or more portions of a supplemental nutrition apparatus may comprise a skin-colored and/or nude material. One or more of a support element, support frame, support structure, unitary support frame, fluid passageway outlet support, support element belt, or any other suitable portion of the supplemental nutrition apparatus may comprise a material having a color (or lack thereof) configured to camouflage portions of the supplemental nutrition apparatus. In various embodiments, a supplemental nutrition apparatus having one or more camouflaged portions may decrease and/or minimize the change that a child becomes distracted during feeding with the supplemental nutrition apparatus.

It will be apparent to those skilled in the art that various modifications and variations can be made in the present disclosure without departing from the spirit or scope of the disclosure. Thus, it is intended that the embodiments described herein cover the modifications and variations of this disclosure provided they come within the scope of the appended claims and their equivalents.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A supplemental nutrition apparatus comprising:
   a reservoir coupled to and in fluid communication with a fluid passageway, wherein the fluid passageway communicates fluid from the reservoir to a fluid passageway outlet; and
   a support element belt that removably adheres to a user's skin, the support element belt comprising:
      an elongated central portion disposed between a first end and a second end;
      a first belt attachment disposed at the first end;
      a second belt attachment disposed at the second end; and
      a fluid passageway fastener disposed on the elongated central portion;
   wherein the elongated central portion traverses the user's areola;
   wherein the first belt attachment is positioned adjacent to a first side of the user's areola;
   wherein the second belt attachment is positioned adjacent to a second side of the user's areola;
   wherein the fluid passageway fastener and at least one of the first belt attachment and the second belt attachment receives the fluid passageway; and
   wherein the fluid passageway fastener positions the fluid passageway outlet proximate to the user's nipple.

2. The supplemental nutrition apparatus of claim 1, further comprising at least one support frame configured to removably secure the supplemental nutrition apparatus to the user's breast and wherein the support frame comprises a sliding mechanism to permit lateral telescopic movement.

3. The supplemental nutrition apparatus of claim 1, wherein the support element belt comprises food-grade, BPA-free materials.

4. The supplemental nutrition apparatus of claim 1, wherein the reservoir comprises a reservoir outlet configured to communicate fluid from the reservoir to the fluid passageway.

5. The supplemental nutrition apparatus of claim 4, wherein the reservoir further comprises at least one guide hook.

6. The supplemental nutrition apparatus of claim 5, wherein the reservoir further comprises a reservoir mounting element.

7. The supplemental nutrition apparatus of claim 6, wherein the reservoir further comprises a filter configured to separate solids from fluid nutrition communicated into the fluid passageway.

8. The supplemental nutrition apparatus of claim 1, further comprising an attachment element disposed on the reservoir and configured to removably couple the supplemental nutrition apparatus to the user.

9. The supplemental nutrition apparatus of claim 1,
   wherein the fluid passageway outlet is further positioned to be brought into a child's mouth during use of the supplemental nutrition apparatus;
   wherein an adhesive is disposed on a portion of the support belt element that adheres to the user's skin; and
   wherein the first belt attachment and the second belt attachment are are disposed away from the user's skin such that the adhesive is not brought into the child's mouth during use of the supplemental nutrition apparatus.

10. The supplemental nutrition apparatus of claim 1, wherein the fluid passageway fastener comprises an aperture disposed in and defined by the elongated central portion.

11. The supplemental nutrition apparatus of claim 10, wherein the fluid passageway fastener comprises a clip, clasp, snap, or any other fastener suitable for coupling the fluid passageway to the elongated central portion, and is configured to be disposed in a child's mouth during use of the supplemental nutrition apparatus.

12. The supplemental nutrition apparatus of claim 9, wherein the adhesive is disposed on a back side of the first belt attachment and the second belt attachment.

13. The supplemental nutrition apparatus of claim 1, wherein the support element belt is low-profile.

14. The supplemental nutrition apparatus of claim 2, wherein the first belt attachment and the second belt attachment comprise at least one of apertures, clips, clasps, and hooks, and wherein the first belt attachment and the second belt attachment are configured to couple the support element belt to the support frame.

15. The supplemental nutrition apparatus of claim 1,
   wherein the fluid passageway comprises a proximal end connected to the reservoir and a distal end, wherein the distal end comprises an angled portion configured to to facilitate latching of a child to the user's nipple during use of the supplemental nutrition apparatus.

16. The supplemental nutrition apparatus of claim 6, wherein the reservoir mounting element is configured to slide over a bra strap and reversibly snap closed.

\* \* \* \* \*